(12) United States Patent
Tsai et al.

(10) Patent No.: US 11,420,953 B2
(45) Date of Patent: Aug. 23, 2022

(54) CO-CRYSTAL AND/OR EUTECTIC CRYSTAL OF KOJIC ACID, COMPOSITIONS COMPRISING THE SAME, PROCESS OF PRODUCING THE SAME, AND USES THEREOF

(71) Applicant: SyneuRx International (Taiwan) Corp., New Taipei (TW)

(72) Inventors: Guo-Chuan Emil Tsai, New Taipei (TW); Ching-Cheng Wang, New Taipei (TW); Tien-Lan Hsieh, New Taipei (TW)

(73) Assignee: SYNEURX INTERNATIONAL (TAIWAN) CORP., New Taipei (TW)

( * ) Notice: Subject to any disclaimer, the term of this patent is extended or adjusted under 35 U.S.C. 154(b) by 61 days.

(21) Appl. No.: 16/337,935

(22) PCT Filed: Sep. 18, 2017

(86) PCT No.: PCT/CN2017/102018
§ 371 (c)(1),
(2) Date: Mar. 29, 2019

(87) PCT Pub. No.: WO2018/059257
PCT Pub. Date: Apr. 5, 2018

(65) Prior Publication Data
US 2020/0247771 A1    Aug. 6, 2020

(51) Int. Cl.
*C07D 309/40* (2006.01)
(52) U.S. Cl.
CPC ........ *C07D 309/40* (2013.01); *C07B 2200/13* (2013.01)
(58) Field of Classification Search
CPC .................................................. C07D 309/40
See application file for complete search history.

(56) References Cited

U.S. PATENT DOCUMENTS

| 66,277,646 | * | 9/2003 | Bakale | A61P 37/08 514/322 |
| 2012/0245135 A1 | * | 9/2012 | Thottathil | A61P 31/04 514/188 |

OTHER PUBLICATIONS

Layzer et al., "Section Five-Degenerative, etc.," Cecil Textbook of Medicine, 20th edition, vol. 2, pp. 2050-2057. (Year: 1996).*
Concise Encyclopedia Chemistry, NY: Walter de Gruyter, 872-873. (Year: 1993).*
U.S. Pharmacopia #23, National Formulary #18, 1843-1844. (Year: 1995).*
Halebian et al., "Pharmaceutical Applications,etc.," Pharmaceutical Sciences 58(8), 911-929. (Year: 1969).*
Sekhon BS, "Pharmaceutical co-crystals, etc.," Ars Pharm., 50(2): 99-117. (Year: 2009).*
Kirk-Othmer Encyclopedia of Chemical Technology, 8, pp. 95-147 . (Year: 2002).*

* cited by examiner

*Primary Examiner* — Patricia L Morris

(57) ABSTRACT

Novel co-crystal and eutectic crystal of kojic acid and a co-former that are excellent in physical properties are provided. In one aspect, novel co-crystals of kojic acid and a co-former that is maltol or ethyl maltol are provided. In another aspect, novel crystal of a eutectic mixture of kojic acid and a co-former that is selected from the group consisting of, maltol, ethyl maltol, methyl paraben and propyl gallate are provided. Methods for producing the novel co-crystal or eutectic crystal are also described. The novel co-crystals and eutectic crystals may be included in a pharmaceutical composition, a health food product or a medical food product for the treatment and/or prophylaxis of a neuropsychiatric disorder.

6 Claims, 10 Drawing Sheets

CO-CRYSTAL AND/OR EUTECTIC CRYSTAL OF KOJIC ACID, COMPOSITIONS COMPRISING THE SAME, PROCESS OF PRODUCING THE SAME, AND USES THEREOF

CROSS-REFERENCES TO RELATED APPLICATIONS

This application relates to and claims the benefit of U.S. Provisional Application No. 62/401,193, filed Sep. 29, 2016; the content of which is incorporated herein by reference in its entirety.

BACKGROUND OF THE INVENTION

1. Field of the Invention

The present disclosure relates to a novel co-crystal and/or eutectic crystal of kojic acid that is excellent in physical property; and methods of producing the same.

2. Description of Related Art kojic acid or 5-hydroxy-2-(hydroxymethyl)-4-pyrone, is an organic acid produced biologically by different types of fungi during aerobic fermentation process. Kojic acid has the ability to act as the UV protector, whereby it suppresses hyperpigmentation in human skins by restraining the formation of melanin through the inhibition of tyrosinase formation, the enzyme that is responsible for skin pigmentation (Noh et al., Bioorg. Med. Chem. Lett. (2009) 19, 5586-5589). Thus, the interests in kojic acid have mainly been in the cosmetic and health care industries, in which kojic acid primarily functions as the basic material for the production of skin whitening creams, skin protective lotion and tooth care products. Apart from its main applications in cosmetics, kojic acid is also known to possess antibiotic properties against gram-negative and gram-positive microorganisms. It also exhibits certain insecticidal activity against *Spodoptera frugiperda* insects, and has been employed as a chelating agent for the production of insecticides.

In general, *Aspergillus* spp. is widely used in the fermentation of kojic acid. Various fermentation techniques, such as submerged, solid state, and surface cultures have been developed and used for the improvement of various fermentation processes. Several kojic acid producing strains have been isolated, among them, *A. flavus, A. oryzae, A. tamarii* and *A. parasiticus* were reported to have the ability of producing large amounts of kojic acid.

Further, in the production of drug substance for use as a medicine, it is advantageous to produce the drug substance in crystal form, for crystals are easier to handle while exhibiting improved properties, such as solubility, stability, pharmacokinetic and biological effects.

To date, there is not any reference describing the co-crystal of kojic acid and a co-former, or the crystal of a eutectic mixture of kojic acid and a co-former. Accordingly, it is desired to develop a novel crystalline polymorphic kojic acid and a co-former that is excellent in physical properties including solubility, storage stability and hygroscopicity, as well as reduced in the content of impurities.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

An objective of the present invention is to provide a co-crystal or a eutectic crystal of kojic acid and a co-former. After intensive studies, the inventors of the present invention found that the co-crystal of kojic acid and maltol, the co-crystal of kojic acid and ethyl maltol, and the eutectic crystals of kojic acid and a co-former are excellent in storage stability, hygroscopicity and purity; thus are suitable for use as a drug substance or an active compound of a pharmaceutical composition for treating a neuropsychiatric disorder.

Accordingly, a first aspect of the present disclosure is directed to a co-crystal of kojic acid and maltol in the molecular ratio of 1:1. The co-crystal yields a powder X-ray diffraction pattern characterized in having characteristic peaks of, 13.3, 14.0, 14.2, 14.7, 15.1, 15.4, 16.0, 16.3, 17.4, 17.8, 18.1, 19.3, 21.3, 21.6, 22.0, 23.6, 23.8, 25.3, 25.6, 26.6, 27.0, 27.2, 27.5, 28.0, 28.3, 29.1, 29.7, 30.3, 30.4, 30.8, 30.9, 32.2, 32.9, 33.1, 35.6, 35.7, 36.1, 37.3, 39.1, 39.2, 39.7, 39.8, 44.5, 44.7, 44.8°±0.2° at reflection angle 2θ. Preferably, the co-crystal has a powder X-ray diffraction pattern substantially as depicted in FIG. 1. Further, the co-crystal has an endothermic peak corresponding to the melting point of about 128-130° C.

A second aspect of the present disclosure is directed to a co-crystal of kojic acid and ethyl maltol in the molecular ratio of 2:1. The co-crystal yields a powder X-ray diffraction pattern characterized in having characteristic peaks of, 8.6, 8.8, 13.4, 13.6, 14.2, 15.6, 17.7, 18.4, 19.2, 21.6, 22.0, 23.0, 23.2, 23.5, 24.7, 25.3, 26.4, 26.6, 26.9, 27.3, 27.6, 28.5, 28.6, 29.0, 29.7, 29.9, 30.1, 30.5, 30.6, 31.0, 31.9, 32.0, 32.1, 32.9, 33.8, 35.8, 36.2, 37.3, 39.1, 39.2, 39.9, 40.8, 41.6, 42.7, 42.8, 42.9, 43.5, 43.7, 44.0, 44.5, 44.8, 44.9°±0.2° at reflection angle 2θ. Preferably, the co-crystal has a powder X-ray diffraction pattern substantially as depicted in FIG. 5. Further, the co-crystal has an endothermic peak corresponding to the melting point of about 88-90° C.

A third aspect of the present disclosure is directed to a crystal of a eutectic mixture of kojic acid and a co-former that is any of maltol, ethyl maltol, propyl gallate, or methyl paraben, in the molecular ratio of 2:1.

In the example when the co-former is maltol, the eutectic crystal yields a powder X-ray diffraction pattern characterized in having characteristic peaks of, 14.0, 14.2, 14.7, 19.3, 21.0, 21.5, 22.0, 23.8, 25.3, 26.7, 27.0, 27.5, 27.6, 28.5, 29.1, 30.4, 31.1, 35.6, 35.7, 36.2, 37.4, 39.1, 39.2, 39.6, 41.4, 41.7, 42.8, 44.8, 44.9°±0.2° at reflection angle 2θ. Preferably, the eutectic crystal has a powder X-ray diffraction pattern substantially as depicted in FIG. 9. Further, the eutectic crystal has an endothermic peak corresponding to the melting point of about 125-127° C.

In the example when the co-former is propyl gallate, the eutectic crystal yields a powder X-ray diffraction pattern characterized in having characteristic peaks of, 4.3, 5.1, 5.6, 7.7, 10.2, 10.5, 11.0, 11.8, 13.5, 14.2, 14.8, 15.6, 16.1, 16.3, 16.5, 16.8, 17.2, 17.4, 17.8, 18.6, 19.3, 20.4, 20.7, 21.6, 21.9, 22.6, 23.2, 23.5, 23.8, 25.3, 25.9, 26.3, 26.7, 27.5, 28.5, 29.2, 30.0, 30.4, 31.0, 31.3, 32.1, 33.2, 33.8, 35.0, 35.7, 36.2, 37.4, 37.7, 38.3, 38.8, 39.1, 39.8, 41.6, 42.7, 42.8, 43.6, 44.8°±0.2° at reflection angle 2θ. Preferably, the eutectic crystal has a powder X-ray diffraction pattern substantially as depicted in FIG. 13. Further, the eutectic crystal has an endothermic peak corresponding to the melting point of about 112-114° C.

In the example when the co-former is methyl paraben, the eutectic crystal yields a powder X-ray diffraction pattern characterized in having characteristic peaks of, 8.9, 9.1, 9.6, 10.0, 11.6, 13.7, 14.1, 14.2, 15.1, 15.3, 15.5, 16.6, 16.9, 17.1, 17.4, 17.9, 18.3, 18.5, 18.6, 19.0, 19.1, 19.3, 20.1, 21.0, 21.6, 22.0, 22.9, 23.9, 25.0, 25.1, 25.3, 25.6, 26.0, 26.2, 26.7, 27.6, 27.8, 28.5, 29.2, 29.5, 29.8, 30.5, 30.8, 30.9, 31.0, 31.9, 32.0, 32.2, 32.3, 33.2, 33.3, 33.9, 35.0, 35.5, 35.7, 35.8, 35.9, 36.0, 36.1, 36.4, 36.9, 37.5, 37.9, 38.8, 38.9, 39.2, 39.9, 41.6, 42.4, 42.6, 42.7, 42.8, 43.1, 43.5, 43.6, 44.1, 44.6, 44.9±0.2° at reflection angle 2θ. Preferably, the eutectic crystal has a powder X-ray diffraction pattern substantially as depicted in FIG. 17. Further, the eutectic crystal has an endothermic peak corresponding to the melting point of about 117-119° C.

Preferably, the co-crystal or the eutectic crystal is substantially pure with a level of impurity that is less than 3%, most preferably, less than 1%. Accordingly, the co-crystal or the eutectic crystal is suitable for use as a drug substance for manufacturing a medicament, a health food product or a medical food product. The medicament, the health food product or the medical food product comprising the present co-crystal or eutectic crystal is suitable for ameliorating symptoms associated with a neuropsychiatric disorder. Examples of neuropsychiatric disorder include, but are not limited to, schizophrenia, anxiety, social anxiety disorder, panic disorder, pain, Alzheimer's disease, dementia, mild cognitive impairment, autism, Asperger's disorder, depression, attention deficit hyperactivity disorder (ADHD), obsessive compulsive disorder, benign forgetfulness, childhood learning disorders, closed head injury, premenstrual syndrome and bipolar disorder.

Another objective of the present invention is to provide a method for producing the co-crystal or the eutectic crystal as described above. The method includes steps of, (a) dissolving the mixture of kojic acid and a co-former (e.g., maltol) at a first temperature until it's molten; (b) adding a solvent in a drop-wise manner to the molten mixture of the step (a) until a solution is formed; heating the solution of the step (b) to a second temperature; and (c) cooling the heated solution of step (c) to ambient temperature to form the co-crystal or the eutectic crystal; wherein the second temperature is higher than the first temperature. Optionally, the method may further include the steps of, washing the co-crystal or the eutectic crystal with the solvent; and drying the washed co-crystal or eutectic crystal.

Examples of the solvent that may be used in the present method include, but are not limited to, methanol, ethanol, isopropanol, butanol, acetone, ethyl acetate, isopropyl acetate, dichloromethane, 1,2-dichloroethane and acetonitrile. Preferably, the solvent is methanol.

Examples for the co-former that may be used in the present method include, but are not limited to, a kojic acid derivatives such as maltol, ethyl maltol, 5-hydroxymaltol, and isomaltol; $C_{2-6}$ dicarboxylic acid such as oxalic acid, malonic acid, tartaric acid, fumaric acid, succinic acid, maleic acid, malic acid, glutaric acid, and adipic acid; $C_{2-7}$ monocarboxylic acid such as acetic acid, glycolic acid, lactic acid, propionic acid, sorbic acid, and benzoic acid; amino acid such as glycine, cysteine, aspartic acid, and leucine; multi-carboxylic acid such as citric acid and pentetic acid; polyols such as butylene glycol, propylene glycol, glycerin, mannitol, sorbitol, xylitol, maltitol, and erythritol; dihydroxyfuranone such as ascorbic acid and erythorbic acid; ketohexoses such as tagatose; nicotinamide; phenylmercuric acetate; thimerosal; neotame; propyl gallate; methyl paraben; and saccharin. Preferably, the co-former is maltol or ethyl maltol.

In one preferred example, the co-former is maltol, and the co-crystal has a powder X-ray diffraction pattern comprising characteristic peaks of, 13.3, 14.0, 14.2, 14.7, 15.1, 15.4, 16.0, 16.3, 17.4, 17.8, 18.1, 19.3, 21.3, 21.6, 22.0, 23.6, 23.8, 25.3, 25.6, 26.6, 27.0, 27.2, 27.5, 28.0, 28.3, 29.1, 29.7, 30.3, 30.4, 30.8, 30.9, 32.2, 32.9, 33.1, 35.6, 35.7, 36.1, 37.3, 39.1, 39.2, 39.7, 39.8, 44.5, 44.7, 44.8°±0.2° at reflection angle 2θ. Preferably, the co-crystal has a powder X-ray diffraction pattern substantially as depicted in FIG. 1.

In another preferred example, the co-former is ethyl maltol, and the co-crystal has a powder X-ray diffraction pattern comprising characteristic peaks of, 8.6, 8.8, 13.4, 13.6, 14.2, 15.6, 17.7, 18.4, 19.2, 21.6, 22.0, 23.0, 23.2, 23.5, 24.7, 25.3, 26.4, 26.6, 26.9, 27.3, 27.6, 28.5, 28.6, 29.0, 29.7, 29.9, 30.1, 30.5, 30.6, 31.0, 31.9, 32.0, 32.1, 32.9, 33.8, 35.8, 36.2, 37.3, 39.1, 39.2, 39.9, 40.8, 41.6, 42.7, 42.8, 42.9, 43.5, 43.7, 44.0, 44.5, 44.8, 44.9±0.2° at reflection angle 2θ. Preferably, the co-crystal has a powder X-ray diffraction pattern substantially as depicted in FIG. 5.

In a further example, the co-former is maltol, which forms an eutectic crystal with kojic acid, and the eutectic crystal has a powder X-ray diffraction pattern comprising characteristic peaks of, 14.0, 14.2, 14.7, 19.3, 21.0, 21.5, 22.0, 23.8, 25.3, 26.7, 27.0, 27.5, 27.6, 28.5, 29.1, 30.4, 31.1, 35.6, 35.7, 36.2, 37.4, 39.1, 39.2, 39.6, 41.4, 41.7, 42.8, 44.8, 44.9±0.2° at reflection angle 2θ. Preferably, the eutectic crystal has a powder X-ray diffraction pattern substantially as depicted in FIG. 9.

In still a further example, the co-former is propyl gallate, which forms a eutectic mixture with kojic acid, and the eutectic crystal has a powder X-ray diffraction pattern comprising characteristic peaks of, 4.3, 5.1, 5.6, 7.7, 10.2, 10.5, 11.0, 11.8, 13.5, 14.2, 14.8, 15.6, 16.1, 16.3, 16.5, 16.8, 17.2, 17.4, 17.8, 18.6, 19.3, 20.4, 20.7, 21.6, 21.9, 22.6, 23.2, 23.5, 23.8, 25.3, 25.9, 26.3, 26.7, 27.5, 28.5, 29.2, 30.0, 30.4, 31.0, 31.3, 32.1, 33.2, 33.8, 35.0, 35.7, 36.2, 37.4, 37.7, 38.3, 38.8, 39.1, 39.8, 41.6, 42.7, 42.8, 43.6, 44.8±0.2° at reflection angle 2θ. Preferably, the eutectic crystal has a powder X-ray diffraction pattern substantially as depicted in FIG. 13.

In yet another example, the co-former is methyl paraben, which also forms a eutectic crystal with kojic acid, and the eutectic crystal has a powder X-ray diffraction pattern comprising characteristic peaks of, 8.9, 9.1, 9.6, 10.0, 11.6, 13.7, 14.1, 14.2, 15.1, 15.3, 15.5, 16.6, 16.9, 17.1, 17.4, 17.9, 18.3, 18.5, 18.6, 19.0, 19.1, 19.3, 20.1, 21.0, 21.6, 22.0, 22.9, 23.9, 25.0, 25.1, 25.3, 25.6, 26.0, 26.2, 26.7, 27.6, 27.8, 28.5, 29.2, 29.5, 29.8, 30.5, 30.8, 30.9, 31.0, 31.9, 32.0, 32.2, 32.3, 33.2, 33.3, 33.9, 35.0, 35.5, 35.7, 35.8, 35.9, 36.0, 36.1, 36.4, 36.9, 37.5, 37.9, 38.8, 38.9, 39.2, 39.9, 41.6, 42.4, 42.6, 42.7, 42.8, 43.1, 43.5, 43.6, 44.1, 44.6, 44.9±0.2° at reflection angle 2θ. Preferably, the eutectic crystal has a powder X-ray diffraction pattern substantially as depicted in FIG. 17.

The novel crystal or eutectic crystal of kojic acid produced by the present method may be included in a pharmaceutic composition, a health food product or a medical food product for ameliorating symptoms associated with a neuropsychiatric disorder. Accordingly, a further objective of the present invention is to provide a composition suitable for use as a pharmaceutical composition, a health food product or a medical food product for ameliorating symptoms associated with a neuropsychiatric disorder. The composition comprises an effective amount of any of the co-crystal or eutectic crystal of the present disclosure; and a suitable carrier.

Accordingly, another objective of the present invention is to provide a method for the treatment or prophylaxis of a subject having or suspected of having a neuropsychiatric disorder. The method includes the step of, administering to the subject the present crystal or eutectic crystal of kojic acid to ameliorate or prevent the symptoms of the neuropsychiatric disorder.

Examples of the neuropsychiatric disorder that may be treated by the present pharmaceutical composition include, but are not limited to, any of schizophrenia, anxiety, social anxiety disorder, panic disorder, pain, Alzheimer's disease, dementia, mild cognitive impairment, autism, Asperger's disorder, depression, attention deficit hyperactivity disorder, obsessive compulsive disorder, childhood learning disorders, closed head injury, premenstrual syndrome or bipolar disorder.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
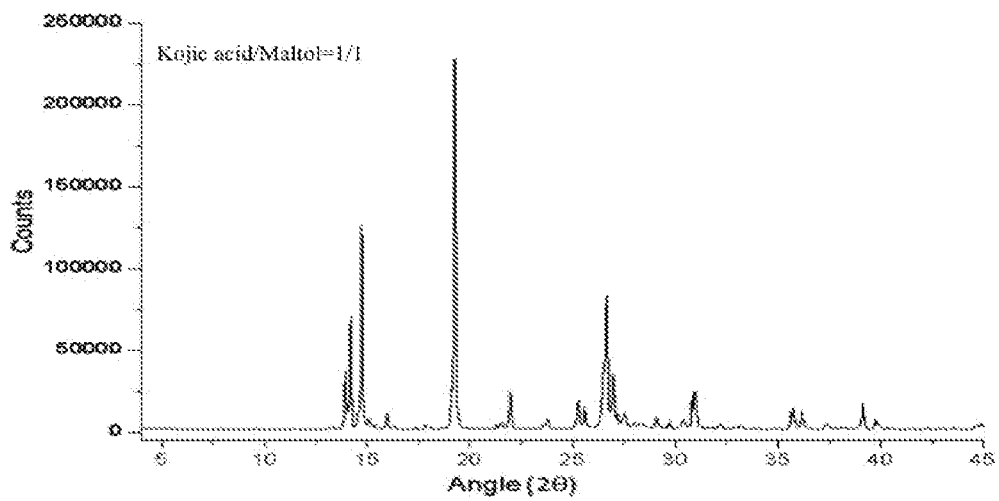
FIG. 1 is the graph illustrating the powder X-ray diffraction analysis of the co-crystals of kojic acid and maltol of Example 1 of this invention.
Figure 2:
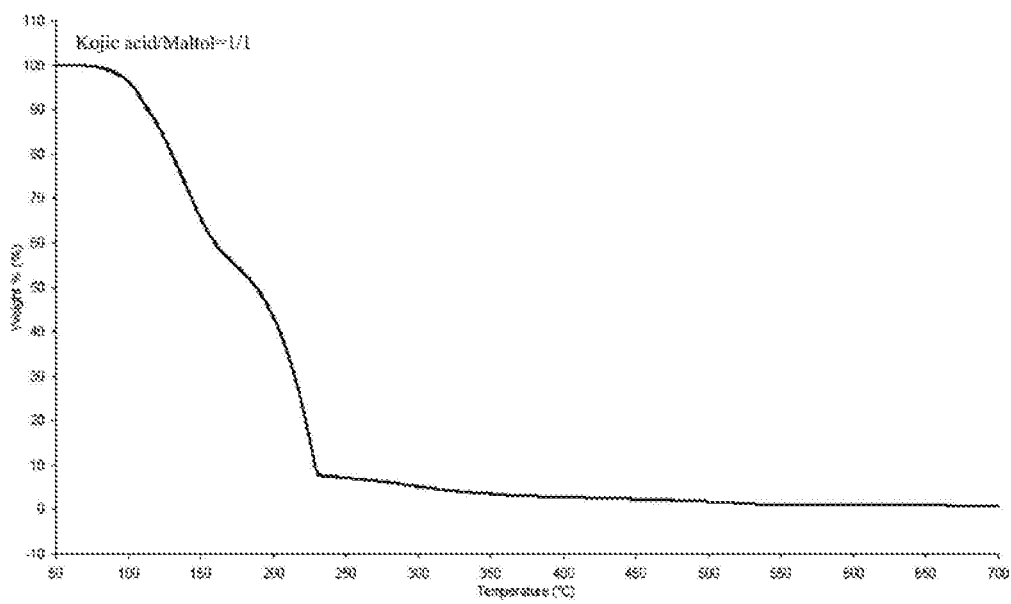
FIG. 2 is the graph illustrating the thermogravimetric analysis (TGA) of the co-crystals of kojic acid and maltol of Example 1 of this invention.
Figure 3:
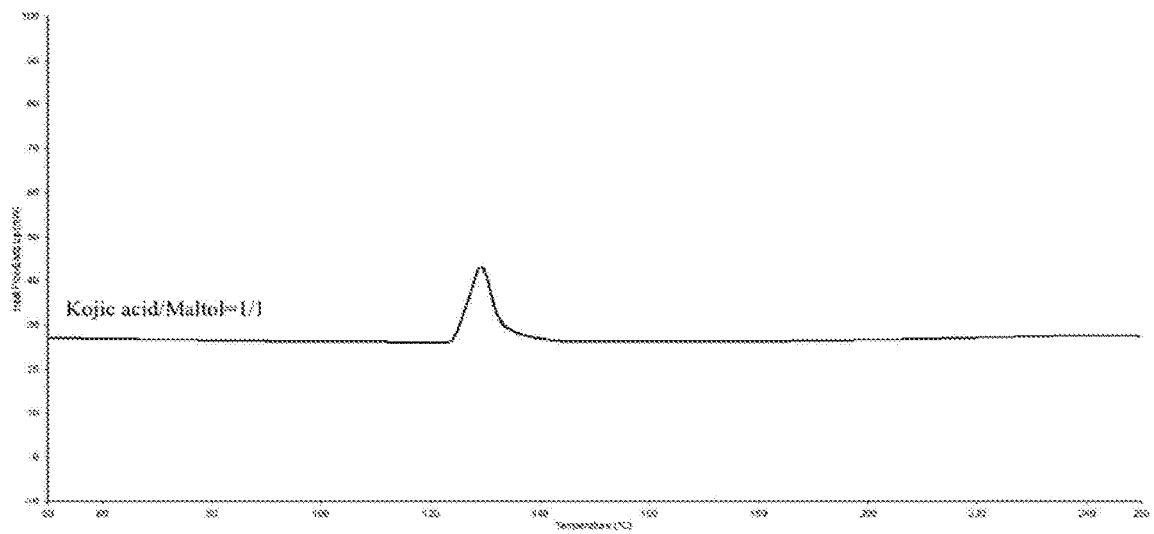
FIG. 3 is the graph illustrating the Differential scanning calorimetry (DSC) analysis of the co-crystals of kojic acid and maltol of Example 1 of this invention.
Figure 4:
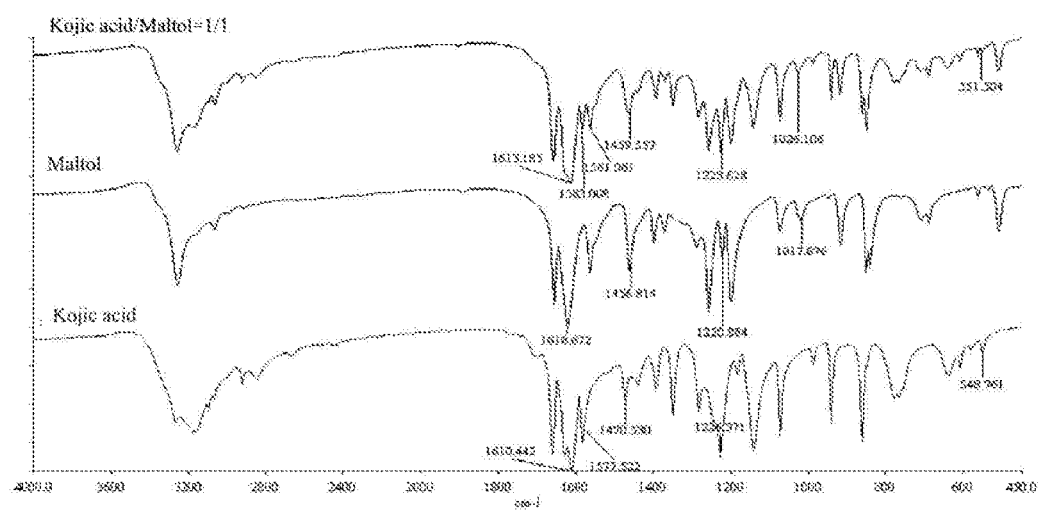
FIG. 4 is the graph illustrating the infrared (IR) analysis of the co-crystals of kojic acid and maltol of Example 1 of this invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definition

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "co-crystal" as used herein refers to a crystalline consists of two or more molecules that form a unique crystalline structure having unique properties. Preferably, the co-crystal of the present disclosure refers to a crystalline consists of kojic acid and a co-crystal former that is not a solvent molecule. According to embodiments of the present disclosure, examples of the co-crystal former include, but are not limited to, a kojic acid derivative such as maltol, ethyl maltol, 5-hydroxymaltol, and isomaltol; $C_{4-6}$ dicarboxylic acid such as oxalic acid, malonic acid, tartaric acid, fumaric acid, succinic acid, maleic Acid, malic acid, glutaric acid, and adipic acid; $C_{2-7}$ monocarboxylic acid such as acetic acid, glycolic acid, lactic acid, propionic acid, sorbic acid, and benzoic acid; amino acid such as glycine, cysteine, aspartic acid, and leucine; multi-carboxylic acid such as citric acid and pentetic acid; polyols such as butylene glycol, propylene glycol, glycerin, mannitol, sorbitol, xylitol, maltitol, and erythritol; dihydroxyfuranone such as ascorbic acid and erythorbic acid; Ketohexoses such as tagatose; nicotinamide; phenylmercuric acetate; thimerosal; neotame; tagatose; propyl gallate; methyl paraben; and saccharin. In one example, the co-crystal former is maltol, which forms a co-crystal with kojic acid in the molecular ratio of 1:1. In another example, the co-crystal former is ethyl maltol, which forms a co-crystal with kojic acid in the molecular ratio of 1:2.

The term "eutectic crystal" as used herein refers a crystalline containing at least two or more molecules that displays on a plot of melting temperature versus relative composition at least one minimum point associated with a homogeneous solid phase, such a point synonymously denoted as a eutectic point or eutectic temperature. Preferably, the eutectic crystal of the present disclosure refers to a crystalline consists of kojic acid and the co-crystal former as described above. In one example, the co-crystal former is maltol, which forms a eutectic crystal with kojic acid in the molecular ratio of 1:2. In another example, the co-crystal former is propyl gallate, which forms a eutectic crystal with kojic acid in the molecular ratio of 1:2. In a further example, the co-crystal former is methyl paraben, which forms a eutectic crystal with kojic acid in the molecular ratio of 1:2.

The term "treating" encompasses partially or completely preventing, ameliorating, mitigating and/or managing a symptom, a secondary disorder or a condition associated with a neuropsychiatric disorder. The term "treating" as used herein refers to application or administration of a pharmaceutical composition comprising the co-crystal or the eutectic crystal prepared in accordance with the method of the present disclosure to a subject, who has a symptom associated with a neuropsychiatric disorder, a disorder secondary to the neuropsychiatric disorder, or a predisposition toward the neuropsychiatric disorder, with the purpose to partially or completely alleviate, ameliorate, relieve, delay onset of, inhibit progression of, reduce severity of, and/or reduce incidence of one or more symptoms, secondary disorders or features of the neuropsychiatric disorder. Treatment may be administered to a subject who exhibits only early signs of such symptoms, disorder, and/or condition for the purpose of decreasing the risk of developing the symptoms, secondary disorders, and/or conditions associated with the neuropsychiatric disorder. Treatment is generally "effective" if one or more symptoms or clinical markers are reduced as that term is defined herein. Alternatively, a treatment is "effective" if the progression of a symptom, disorder or condition is reduced or halted.

The term "effective amount" as used herein refers to the quantity of a component or medicament which is sufficient to yield a desired "effective treatment" as defined hereinabove. The specific effective amount will vary with factors such as the particular condition being treated, the physical condition of the patient (e.g., the patient's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects. Effective amount may be expressed, for example, as the total mass of the medicament (e.g., in grams, milligrams or micrograms) or a ratio of mass of the medicament to body mass, e.g., as milligrams per kilogram (mg/kg). Persons having ordinary skills could calculate the human equivalent dose (HED) for the medicament (such as the co-crystal of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to an animal including the human species that is treatable with the co-crystal or the eutectic crystal of the present disclosure in accordance with the methods of the present disclosure. The term "subject" is intended to refer to both the male and female gender unless one gender is specifically indicated, and may be any age, e.g., a child or adult.

The subject invention provides co-crystals or eutectic crystals of kojic acid and a co-former (e.g., maltol); methods for producing the same; and methods for the treatment or prophylaxis of a subject suffering from a neuropsychiatric disorder.

The co-crystal or eutectic crystals of the present invention can be obtained by any known crystallization processes, which include but are not limited to, solvent evaporation, solvent drop grinding and a slurry crystallization process; and typical examples thereof are provided below.

The compound of the present invention, kojic acid or 5-hydroxy-2-(hydroxymethyl)-4-pyrone, can be produced from various carbohydrate sources in an aerobic fermentation process by a variety of microorganisms, however, it has proven that the batch submerged fermentation gives the highest efficiency in terms of yield, maximum kojic acid concentration and overall productivities (Mohamad et al., Biotecnol. Mol. Biol. Rev. (2010) 5(2): 24-37).

According to embodiments of the present disclosure, kojic acid crystalline, which may be a co-crystal or a eutectic crystal, is formed by evaporating the solvent from a saturated solution of kojic acid and a co-former. Specifically, kojic acid and a co-former are heated to a first temperature to produce a molten mixture, a solvent is then added into the molten mixture in a drop-wise manner until the molten mixture and the solvent becomes a clear solution; the clear solution is then heated to a second temperature, which is higher than the first temperature, to reduce the amount of the solvent therein as well as to help precipitate the crystal; the heating is aborted when crystal starts to form; the thus formed crystalline may then be collected by any suitable means (e.g., filtering).

In preferred embodiments, kojic acid and the co-former is heated to the first temperature between 60-70° C., such as 60, 61, 62, 63, 64, 65, 66, 67, 68, 69, and 70° C. to produce a molten mixture; preferably between 62-68° C., such as 62, 63, 64, 65, 66, 67, and 68° C.; and most preferably at 65° C.

Examples of the solvent that may be added to the molten mixture of kojic acid and the co-former include, but are not limited to, methanol, ethanol, isopropanol, butanol, acetone, ethyl acetate, isopropyl acetate, dichloromethane, 1,2-dichloroethane, acetonitrile, or a mixed solvent of two or more kinds of solvents selected therefrom. In one preferred embodiment, methanol is added in drop wise manner to the molten mixture until a clear solution consists of kojic acid, the co-former and the solvent is produced. The clear solution is then heated to the second temperature between 70-80° C., such as 70, 71, 72, 73, 74, 75, 76, 77, 78, 79, and 80° C., so as to reduce the amount of the solvent therein. The evaporation of solvent would help formation of the crystal. Preferably the clear solution is heated to the temperature between 72-78° C., such as 72, 73, 74, 75, 76, 77, and 78° C.; and most preferably at 75° C. Heating is then aborted when crystal starts to form. Once the heating is ceased, the solution is allowed to cool to ambient temperature (e.g., room temperature) to help formation of the crystal. Optionally, seed crystals may be added to facilitate the crystallization process. The thus formed crystal may then be collected by filtering. Optionally, the collected crystal is washed and dried (e.g., oven dried).

Suitable examples of the co-former to be used in the present disclosure to form co-crystal or eutectic crystal with kojic acid include, but are not limited to, a kojic acid derivative such as maltol, ethyl maltol, 5-hydroxymaltol, and isomaltol; $C_{4-6}$ dicarboxylic acid such as oxalic acid, malonic acid, tartaric acid, fumaric acid, succinic acid, maleic acid, malic acid, glutaric acid, and adipic acid; $C_{2-7}$ monocarboxylic acid such as acetic acid, glycolic acid, lactic acid, propionic acid, sorbic acid, and benzoic acid; amino acid such as glycine, cysteine, aspartic acid, and leucine; multi-carboxylic acid such as citric acid and pentetic acid; polyols such as butylene glycol, propylene glycol, glycerin, mannitol, sorbitol, xylitol, maltitol, and erythritol; dihydroxyfuranone such as ascorbic acid and erythorbic acid; ketohexoses such as tagatose; nicotinamide; phenylmercuric acetate; thimerosal; neotame; tagatose; propyl gallate; methyl paraben; and saccharin. In one example, the co-former is maltol. In another example, the co-former is ethyl maltol.

In some embodiments, co-crystals of kojic acid and the co-former are formed. In other embodiments, eutectic crystals of kojic acid and the co-former are formed. The co-crystals or eutectic crystals of the present invention respectively yield a characteristic powder X-ray diffraction pattern (XRD), and each co-crystal or eutectic crystal has a specific value of 2θ.

In a powder X-ray diffraction pattern, $I_{max}$ denotes an intensity of a peak having a large intensity of a crystal, whereas I denotes an intensity of each peak. The value of 2θ of the powder X-ray diffraction pattern can vary by approximately 0.1° to 0.2° with the state of the sample and measuring conditions. Because of properties of data of the powder X-ray diffraction pattern, general pattern is important for identifying the crystal form. Further, since a relative intensity can slightly vary with the growth direction of crystals, size of particles and/or measuring conditions, the intensity values in the XRD pattern should not be strictly interpreted.

The co-crystal of kojic acid and maltol yields a powder X-ray diffraction pattern having characteristic peaks selected from the group consisting of, 13.3, 14.0, 14.2, 14.7, 15.1, 15.4, 16.0, 16.3, 17.4, 17.8, 18.1, 19.3, 21.3, 21.6, 22.0, 23.6, 23.8, 25.3, 25.6, 26.6, 27.0, 27.2, 27.5, 28.0, 28.3, 29.1, 29.7, 30.3, 30.4, 30.8, 30.9, 32.2, 32.9, 33.1, 35.6, 35.7, 36.1, 37.3, 39.1, 39.2, 39.7, 39.8, 44.5, 44.7, 44.8°±0.2° at reflection angle 2θ. Specifically, it yields a powder X-ray diffraction pattern as depicted in FIG. 1.

Figure 5:
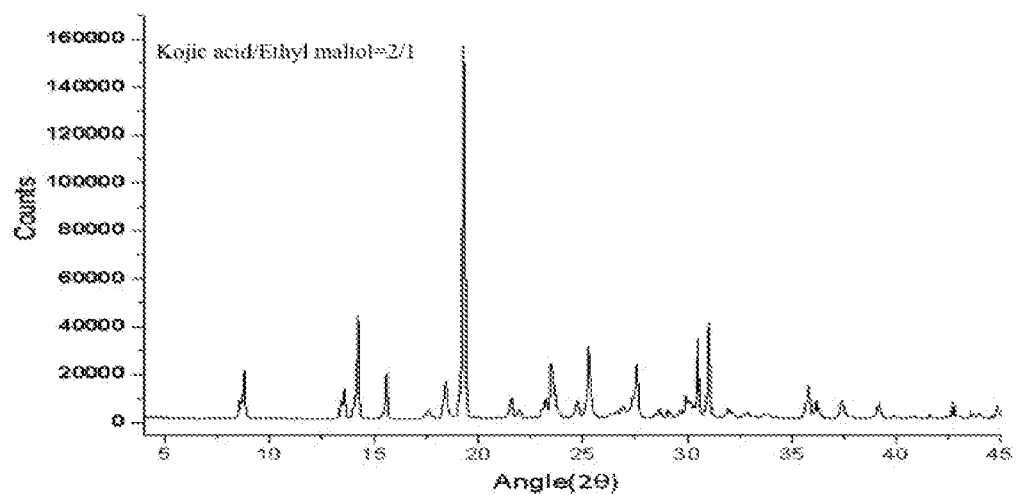
FIG. 5 is the graph illustrating the powder X-ray diffraction analysis of the co-crystals of kojic acid and ethyl maltol of Example 2 of this invention.
Figure 6:
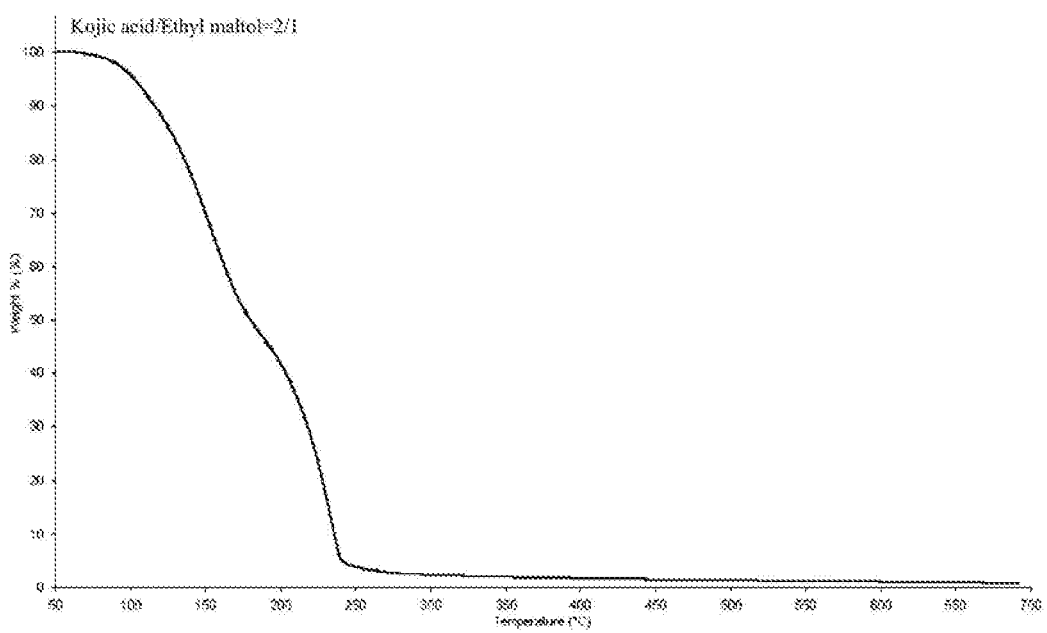
FIG. 6 is the graph illustrating the TGA analysis of the co-crystals of kojic acid and ethyl maltol of Example 2 of this invention.
Figure 7:
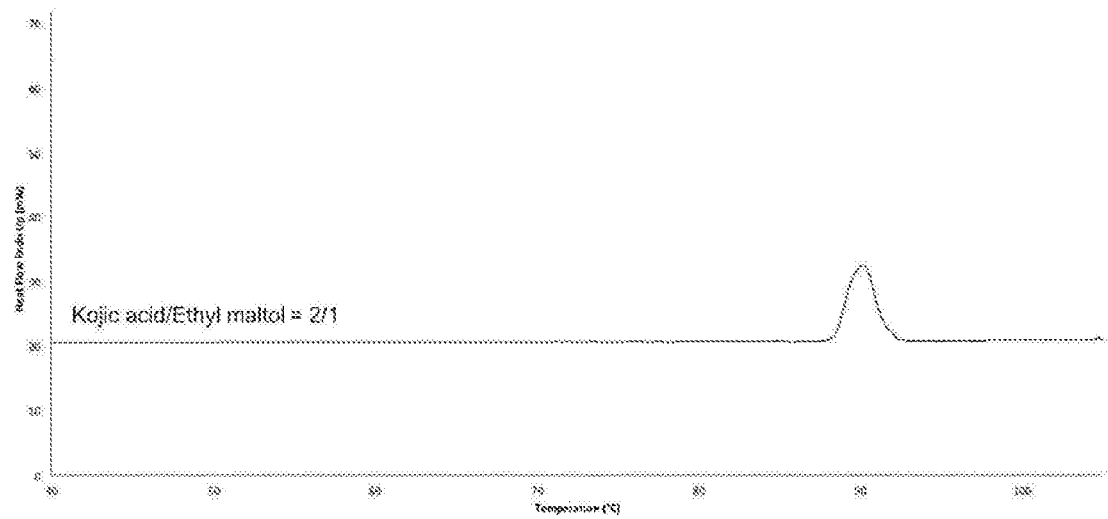
FIG. 7 is the graph illustrating the DSC analysis of the co-crystals of kojic acid and ethyl maltol of Example 2 of this invention.
Figure 8:
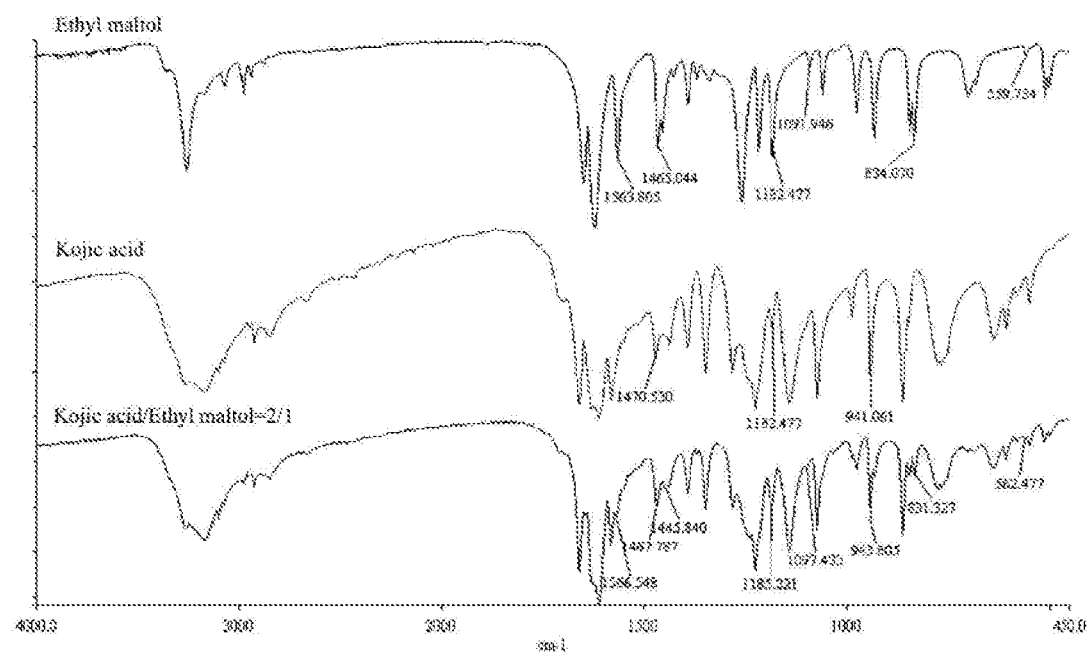
FIG. 8 is the graph illustrating the IR analysis of the co-crystals of kojic acid and ethyl maltol of Example 2 of this invention.

The co-crystalline of kojic acid and ethyl maltol yields a powder X-ray diffraction pattern having characteristic peaks selected from the group consisting of, 8.6, 8.8, 13.4, 13.6, 14.2, 15.6, 17.7, 18.4, 19.2, 21.6, 22.0, 23.0, 23.2, 23.5, 24.7, 25.3, 26.4, 26.6, 26.9, 27.3, 27.6, 28.5, 28.6, 29.0, 29.7, 29.9, 30.1, 30.5, 30.6, 31.0, 31.9, 32.0, 32.1, 32.9, 33.8, 35.8, 36.2, 37.3, 39.1, 39.2, 39.9, 40.8, 41.6, 42.7, 42.8, 42.9, 43.5, 43.7, 44.0, 44.5, 44.8, 44.9±0.2° at reflection angle 2θ. Specifically, it yields a powder X-ray diffraction pattern as depicted in FIG. 5.

Figure 9:
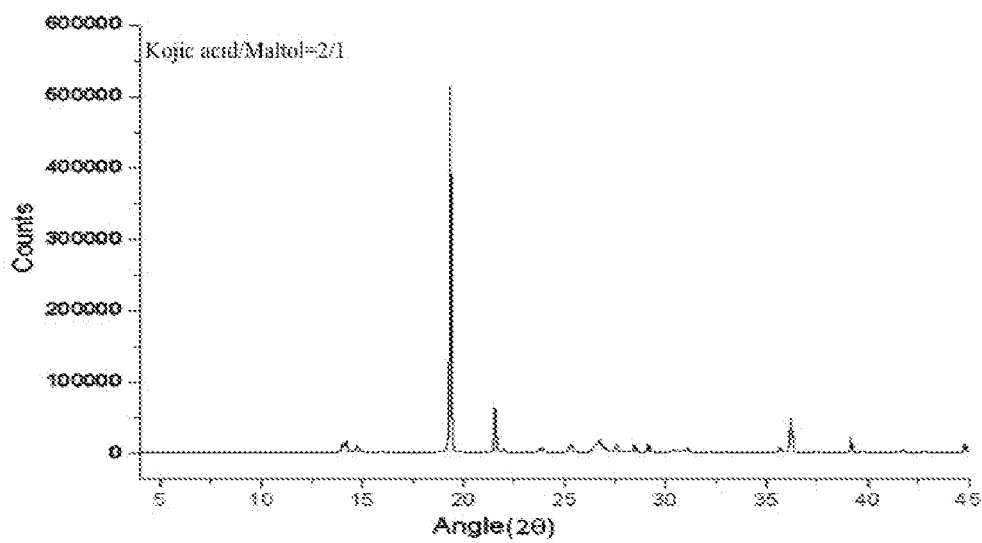
FIG. 9 is the graph illustrating the powder X-ray diffraction analysis of the eutectic crystals of kojic acid and maltol of Example 3 of this invention.
Figure 10:
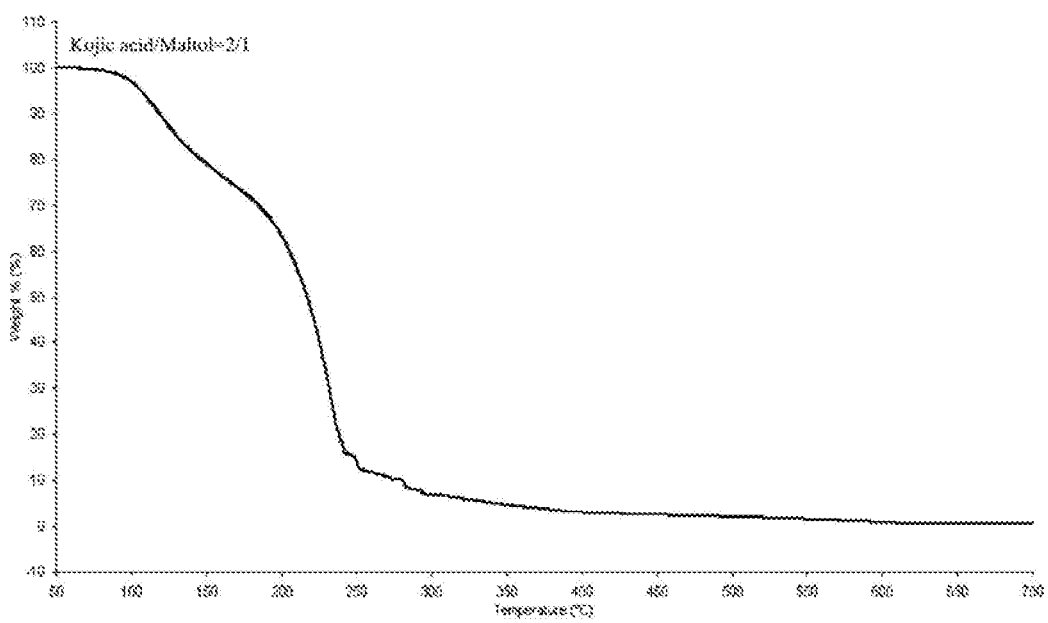
FIG. 10 is the graph illustrating the TGA analysis of the eutectic crystals of kojic acid and maltol of Example 3 of this invention.
Figure 11:
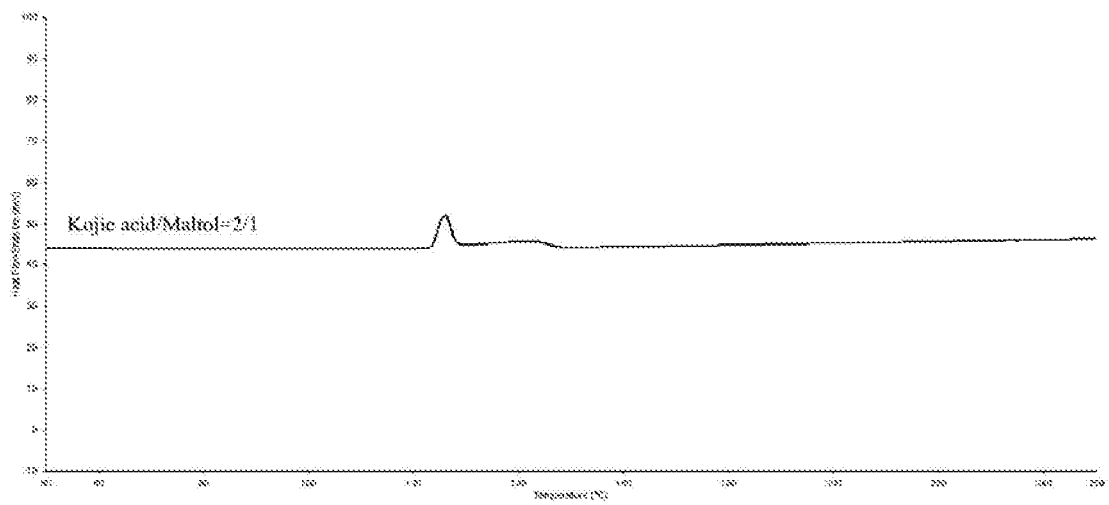
FIG. 11 is the graph illustrating the DSC analysis of the eutectic crystals of kojic acid and maltol of Example 3 of this invention.
Figure 12:
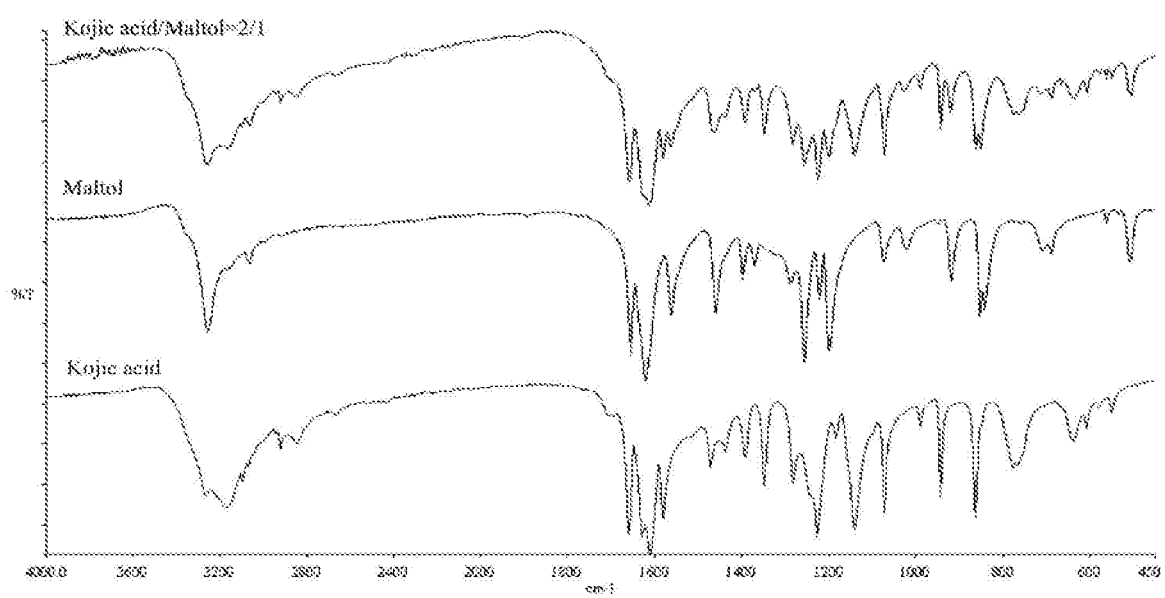
FIG. 12 is the graph illustrating the IR analysis of the eutectic crystals of kojic acid and maltol of Example 3 of this invention.

The eutectic crystals of kojic acid and maltol yields a powder X-ray diffraction pattern characterized in having characteristic peaks of, 14.0, 14.2, 14.7, 19.3, 21.0, 21.5, 22.0, 23.8, 25.3, 26.7, 27.0, 27.5, 27.6, 28.5, 29.1, 30.4, 31.1, 35.6, 35.7, 36.2, 37.4, 39.1, 39.2, 39.6, 41.4, 41.7, 42.8, 44.8, 44.9±0.2° at reflection angle 2θ. Specifically, it yields a powder X-ray diffraction pattern as depicted in FIG. 9.

Figure 13:
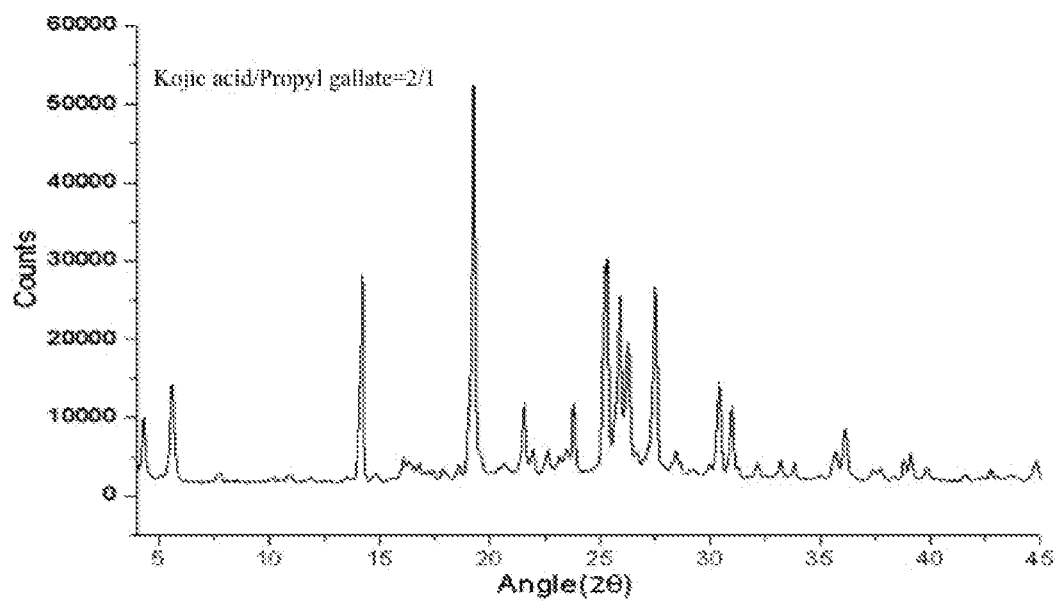
FIG. 13 is the graph illustrating the powder X-ray diffraction analysis of the eutectic crystals of kojic acid and propyl gallate of Example 4 of this invention.
Figure 14:
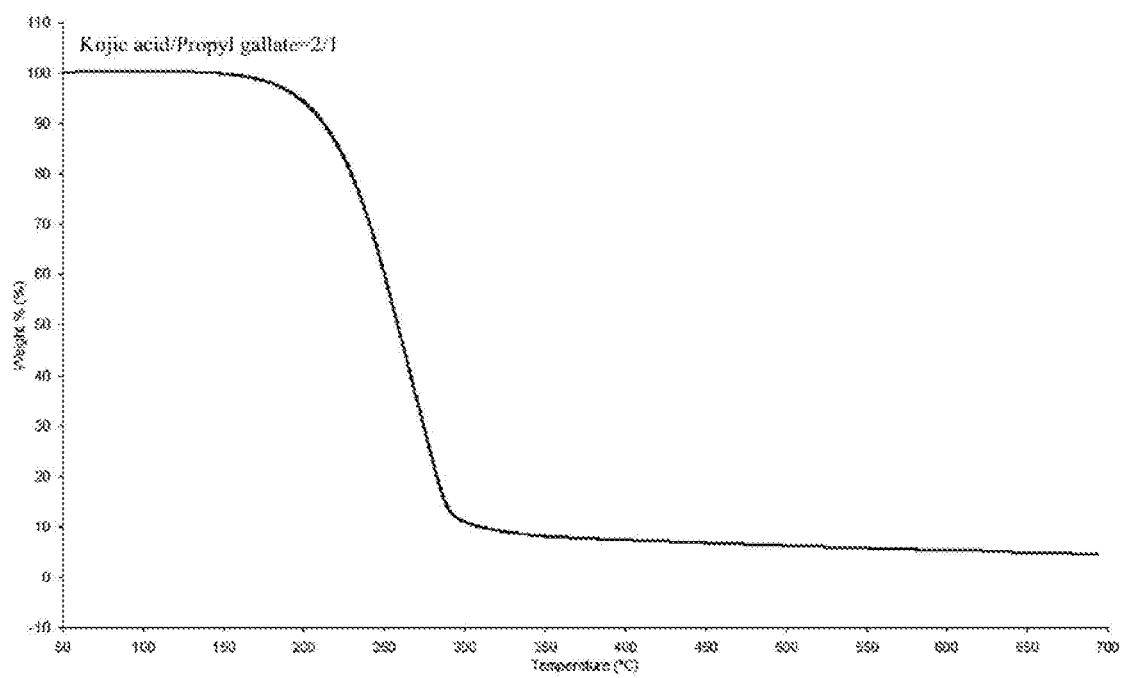
FIG. 14 is the graph illustrating the TGA analysis of the eutectic crystals of kojic acid and propyl gallate of Example 4 of this invention.
Figure 15:
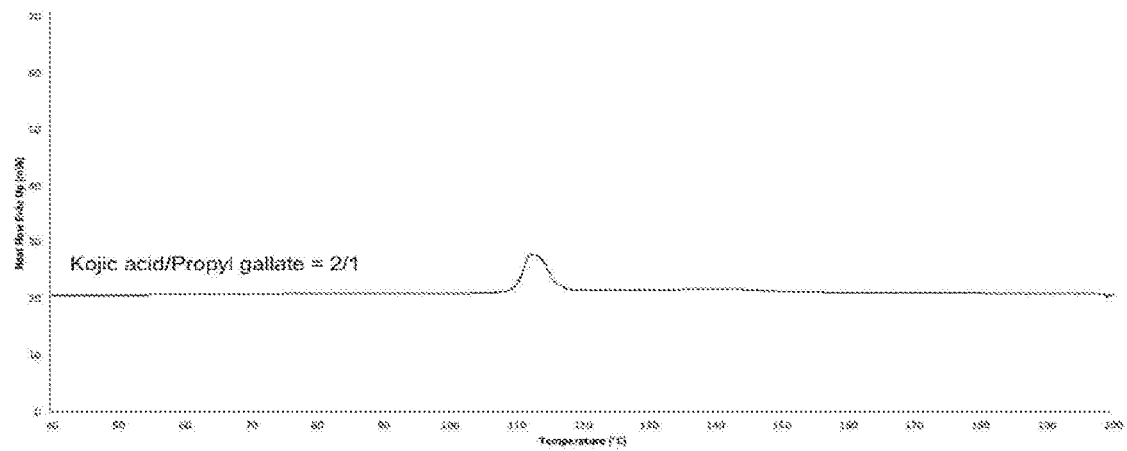
FIG. 15 is the graph illustrating the DSC analysis of the eutectic crystals of kojic acid and propyl gallate of Example 4 of this invention.
Figure 16:
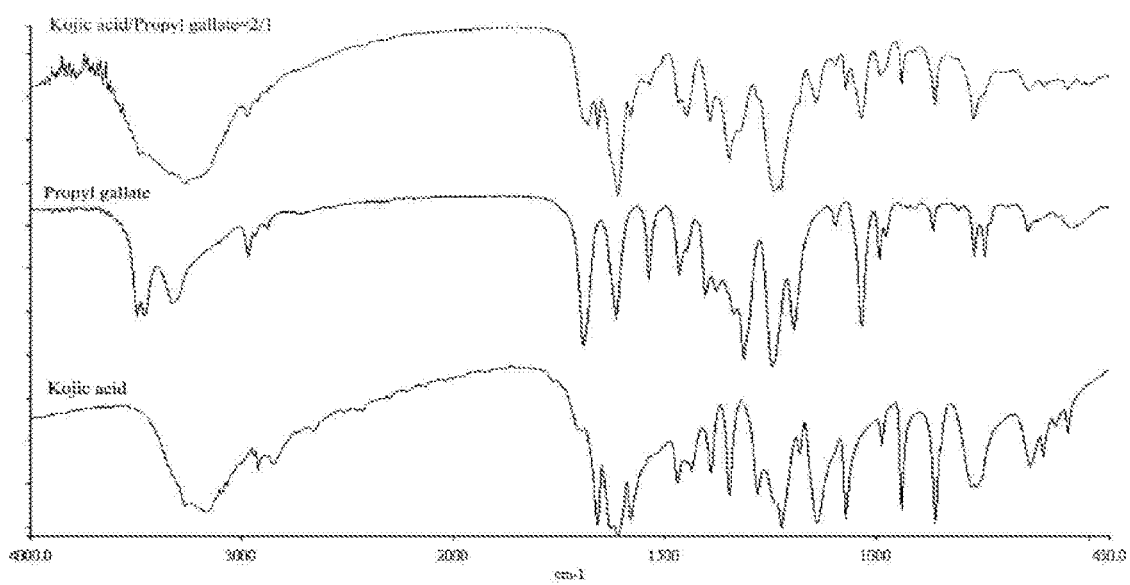
FIG. 16 is the graph illustrating the IR analysis of the eutectic crystals of kojic acid and propyl gallate of Example 4 of this invention.

The eutectic crystals of kojic acid and propyl gallate yields a powder X-ray diffraction pattern characterized in having characteristic peaks of, 4.3, 5.1, 5.6, 7.7, 10.2, 10.5, 11.0, 11.8, 13.5, 14.2, 14.8, 15.6, 16.1, 16.3, 16.5, 16.8, 17.2, 17.4, 17.8, 18.6, 19.3, 20.4, 20.7, 21.6, 21.9, 22.6, 23.2, 23.5, 23.8, 25.3, 25.9, 26.3, 26.7, 27.5, 28.5, 29.2, 30.0, 30.4, 31.0, 31.3, 32.1, 33.2, 33.8, 35.0, 35.7, 36.2, 37.4, 37.7, 38.3, 38.8, 39.1, 39.8, 41.6, 42.7, 42.8, 43.6, 44.8±0.2° at reflection angle 2θ. Specifically, the eutectic crystalline has a powder X-ray diffraction pattern substantially as depicted in FIG. 13.

Figure 17:
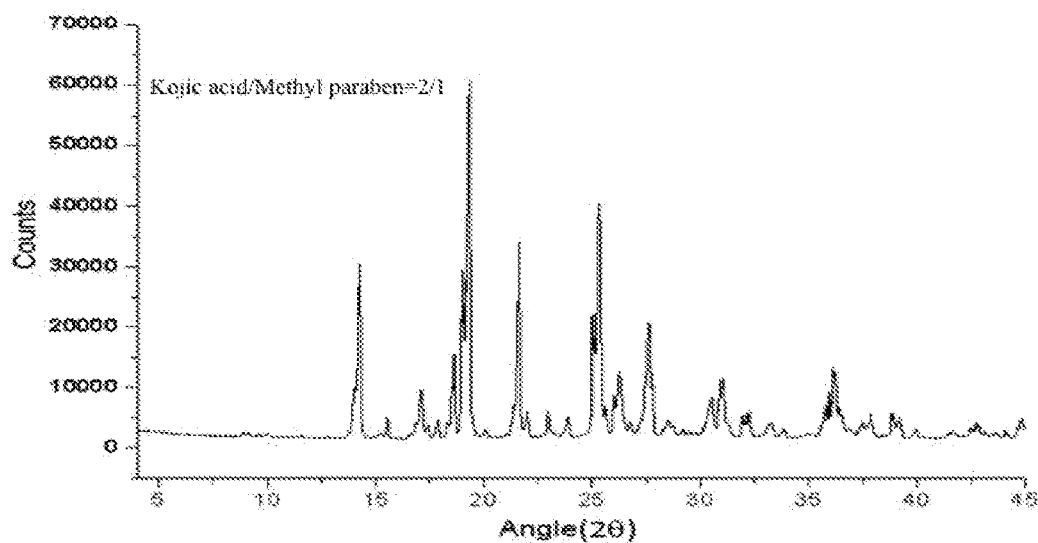
FIG. 17 is the graph illustrating the powder X-ray diffraction analysis of the eutectic crystals of kojic acid and methyl paraben of Example 5 of this invention.
Figure 18:
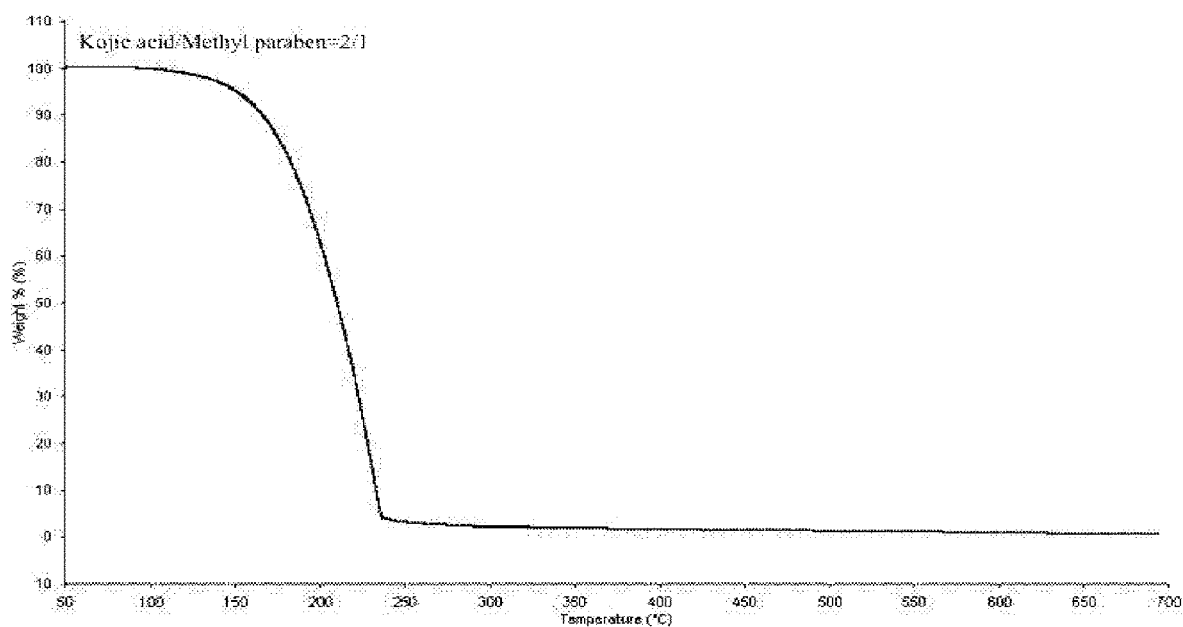
FIG. 18 is the graph illustrating the TGA analysis of the eutectic crystals of kojic acid and methyl paraben of Example 5 of this invention.
Figure 19:
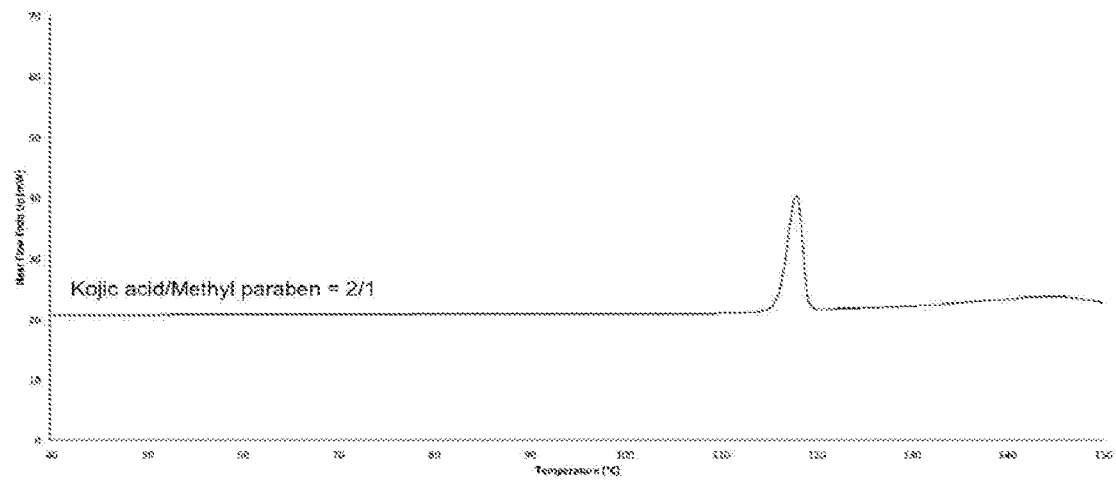
FIG. 19 is the graph illustrating the DSC analysis of the eutectic crystals of kojic acid and methyl paraben of Example 5 of this invention.
Figure 20:
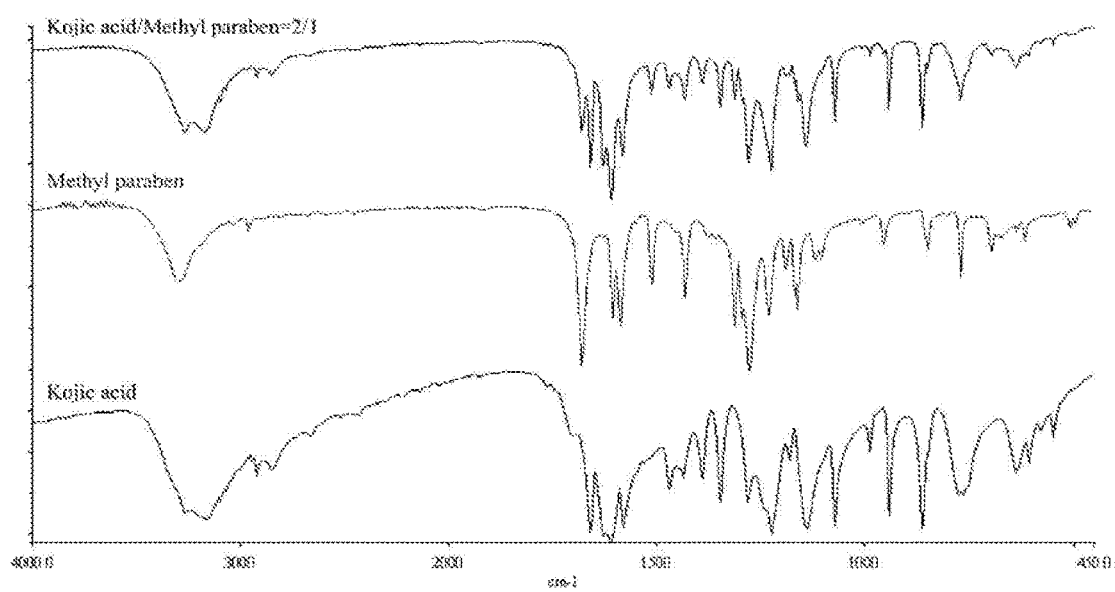
FIG. 20 is the graph illustrating the IR analysis of the eutectic crystals of kojic acid and methyl paraben of Example 5 of this invention.

The eutectic crystals of kojic acid and methyl paraben yields a powder X-ray diffraction pattern characterized in having characteristic peaks of, 8.9, 9.1, 9.6, 10.0, 11.6, 13.7, 14.1, 14.2, 15.1, 15.3, 15.5, 16.6, 16.9, 17.1, 17.4, 17.9, 18.3, 18.5, 18.6, 19.0, 19.1, 19.3, 20.1, 21.0, 21.6, 22.0, 22.9, 23.9, 25.0, 25.1, 25.3, 25.6, 26.0, 26.2, 26.7, 27.6, 27.8, 28.5, 29.2, 29.5, 29.8, 30.5, 30.8, 30.9, 31.0, 31.9, 32.0, 32.2, 32.3, 33.2, 33.3, 33.9, 35.0, 35.5, 35.7, 35.8, 35.9, 36.0, 36.1, 36.4, 36.9, 37.5, 37.9, 38.8, 38.9, 39.2, 39.9, 41.6, 42.4, 42.6, 42.7, 42.8, 43.1, 43.5, 43.6, 44.1, 44.6, 44.9±0.2° at reflection angle 2θ. Specifically, the eutectic crystalline has a powder X-ray diffraction pattern substantially as depicted in FIG. 17.

Impurity of the present co-crystal or eutectic crystal may be verified by high performance liquid chromatography (HPLC) or nuclear magnetic resonance (NMR). According to embodiments of the present disclosure, the impurity level of the co-crystal or eutectic crystal is reduced after the cooling and crystallizing step. Preferably, the impurity level of the co-crystal or eutectic crystal is less than 3%; more preferably, less than 1%; still more preferably, less than 0.5%.

Any co-crystal or eutectic crystal thus obtained can be used as an active ingredient in a medicine, a health food product (e.g., a nutraceutical composition), or a medical food product for ameliorating symptoms associated with a neuropsychiatric disorder.

In the present disclosure, the use of a co-crystal or eutectic crystal is advantageous for handling and storage stability as compared with the case of using no crystal. Particularly, the co-crystal or eutectic crystal is easily handled because of its crystal form, and the purification and drying effect is easily exerted; also, the co-crystal or eutectic crystal is excellent in storage stability, hygroscopicity and purity; thus is useful as an active ingredient of a medicine, a health food product, or a medical food product.

The respective co-crystals or eutectic crystals of the present disclosure may constitute pharmaceutical compositions with pharmaceutical acceptable carriers, and can be administered to a subject orally or parenterally in various dosage forms. Parenterally administration includes, for example, administration by intraveneous, subcutaneous, intramuscular, transdermal, intrarectal, transnasal, intrathecal, and instillation methods.

The dosage form of the pharmaceutical composition for oral administration includes, for example, tablets, pills, granules, powders, solutions, suspensions, syrups or capsules. As a method of producing a tablet, a pill, granule or powder, it can be formed by conventional techniques using a pharmaceutically acceptable carrier such as excipient, binder, or disintegrant and etc. As to the form of a solution, suspension or syrup, it can be produced by conventional techniques using glycerol esters, alcohols, water or vegetable oils, and etc. The form of capsule can be produced by filling a capsule made of gelatin with the granule, powder or a solution prepared as described above. Among the agents for parenteral administration, in the case of intravenous, subcutaneous or intramuscular administration, it can be administered as injection. An injection can be prepared by dissolving the crystal of the present disclosure in water soluble solution such as physiological saline, biodegradable and/or biocompatible copolymer solution, or water insoluble solution consisting of organic esters such as propylene glycol, polyethylene glycol, or vegetable oils. In the case of transdermal administration, for example, a dosage form as an ointment or a cream can be employed. The ointment can be produced by mixing the crystal of the present disclosure with fats or oils and the likes; and the cream can be produced by mixing the crystal of the present disclosure with emulsifiers. In the case of rectal administration, it may be in the form of suppository using a gelatin soft capsule. In the case of transdermal administration, it may be in a form of a liquid or a powdery formulation. In a liquid formulation, water, salt solution, phosphate buffer, acetate buffer and the like may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and the like, and water-unabsorbing materials such as cellulose, starches, gums, or cross-linked polymers. Further, antioxidants, colorants, preservatives may be added to the powdery formulation. The liquid or powdery formulation may be administered by use of a spray apparatus. In case of inhalation through nose or mouth, a solution or suspension containing the crystal of the present disclosure and a pharmaceutical excipient generally accepted for this purpose is inhaled through an inhalant aerosol spray. Alternatively, the crystal of the present disclosure in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

The respective co-crystals or eutectic crystals of the present disclosure may constitute health food products with suitable carriers, and can be administered to a subject orally or parenterally in various dosage forms. In some embodiments, the health food products are in liquid and/or solid/semi-solid forms useful for nourishing humans and animals, for improving basic behavioral functioning, hyperactivity, anxiety, depression, sensorimotor gating, pain threshold, memory and/or cognitive functioning, or for facilitating treatment of any of the target diseases noted herein (e.g., a CNS disorder, including those described herein).

The health food product may be in the form of a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation. The health food product described herein contains the co-crystal or eutectic crystal of kojic acid, and at least one edible carriers that confer one or more of the benefits to the kojic acids in the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, flax seed oil, and/or benzoate.

In some examples, the healthy food product is a nutraceutical composition, which refers to compositions containing components from food sources that confer extra health benefits in addition to the basic nutritional value found in foods, as well as components of a pharmaceutical composition, such as the kojic acid co-crystal or eutectic crystal described herein that ameliorates symptoms associated with a neuropsychiatric disorder. The nutraceutical composition may further include additional ingredients and supplements that promote good health and/or enhance stability and bioactivity of the kojic acids. The actions of nutraceutical compositions may be fast and/or short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for diseases associated with DAAO such as CNS disorders. The nutraceutical compositions may be in the form of a dietary supplement, for such purpose, additional nutrients, such as vitamins, minerals or amino acids may be included. The nutraceutical composition can also be in the form of a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose. The nutraceutical composition disclosed herein can be in the form of a solution. For example, the nutraceutical formulation can be provided in a medium, such as a buffer, a solvent, a diluent, an inert carrier, an oil, or a cream. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets. In some examples, the health food product is in liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof. Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate). The health food products described herein may further comprise one or more second therapeutic agents, including those described herein.

The respective co-crystals or eutectic crystals of the present disclosure may constitute medical food products with suitable carriers, and can be consumed by a subject either orally or enterally to improve the basic behavioral function, hyperactivity, anxiety, depression, sensorimotor gating, pain threshold, memory and/or cognitive functioning, and/or for treating a target disease as described herein (e.g., a CNS disorder). Such food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management.) In some examples, a medical food composition described herein is not one of those that would be simply recommended by a physician as part of an overall diet to manage the symptoms or reduce the risk of a disease or condition.

The medical food composition described herein, which comprises co-crystals or eutectic crystals of kojic acid and at least one carrier (e.g., those described herein), can be in the form of a liquid solution, powder, bar, wafer, a suspension in an appropriate liquid or in a suitable emulsion, as detailed below. The at least one carrier, which can be either naturally-occurring or synthetic (non-naturally occurring), would confer one or more benefits to the kojic acid content in the composition, for example, stability, bioavailability, and/or bioactivity. Any of the carriers described herein may be used to produce the medical food composition. In some embodiments, the medical food composition may further comprise one or more additional ingredients that include, but are not limited to, natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

Accordingly, the present composition suitable for manufacturing a medicament, a health food product or a medical food product suitable for ameliorating symptoms of a neuropsychiatric disorder comprises an effective amount of the co-crystal or eutectic crystal of the present disclosure. The neuropsychiatric disorder may be any of, schizophrenia, anxiety, social anxiety disorder, panic disorder, pain, Alzheimer's disease, dementia, mild cognitive impairment, autism, Asperger's disorder, depression, attention deficit hyperactivity disorder, obsessive compulsive disorder, childhood learning disorders, closed head injury, premenstrual syndrome or bipolar disorder.

According to another feature of the present disclosure, a method of treatment or prevention of a neuropsychiatric disorder in a subject is provided. The method comprises administering to the subject suffering from or susceptible to the neuropsychiatric disorder an effective amount of the co-crystal or eutectic crystal as described herein. The neuropsychiatric disorder treatable by the present method may be any of schizophrenia, anxiety, social anxiety disorder, panic disorder, pain, Alzheimer's disease, dementia, mild cognitive impairment, autism, Asperger's disorder, depression, attention deficit hyperactivity disorder, obsessive compulsive disorder, childhood learning disorders, closed head injury, premenstrual syndrome or bipolar disorder.

The effective amount of the co-crystal or eutectic crystal of the present disclosure suitable for treating any of the afore-mentioned conditions varies with the route of administration, or condition, age, sex, or weight of the subject receiving the treatment. In general, the effective amount is about 1-500 mg/Kg/day, preferably about 10-300 mg/Kg/day in the case of oral administration; whereas it is about 0.1-100 mg/Kg/day, preferably about 0.3-30 mg/Kg/day in the case of intravenous, intramuscular, subcutaneous, transdermal, transnasal, intrarectal, or inhalation.

The present invention will now be described in further detail with reference to the following examples. However, it should be understood that the present invention is not limited to the specified examples.

EXAMPLES

Materials and Methods

Materials. Kojic acid was purchased from Alfa Aesar, and co-crystal formers including maltol, ethyl maltol, methyl paraben and propyl gallate were purchased from Acros and/or Sigma Aldrich.

Crystallization. Crystallization was carried out by cooling a saturated solution. Kojic acid and co-crystal or eutectic crystal former (e.g., maltol, ethyl maltol, methyl paraben or propyl gallate) were mixed in the indicated molar ratio (e.g., 1:1, or 2:1) and the mixture was heated in a water bath at a temperature between 60-65° C., a solvent (e.g., methanol or ethanol) was then added in a drop wise manner into the heated mixture until all powders were dissolved. The mixture was heated again at an elevated temperature about 70-75° C. with stirring, the heating and stirring were discontinued when crystalline started to form. The solution was allowed to cool to room temperature, and the crystalline was collected by filtering, then washed with its mother liquid before subjecting it to dry at room temperature or at an elevated temperature (e.g., 60° C.) in the oven for overnight.

Thermogravimetric (TGA) Analysis

TGA analysis was performed by use of Pyris 1 TGA (Perkin Elmer) over the range of 50° C./700° C. with a gradient of 10° C./min.

Differential Scanning Calorimetry (DSC) Analysis

The melting point of the crystal was determined using DSC method over the range of 50° C./450° C. with a gradient of 10° C./min under nitrogen purge, and the presence or absence of endotherm peaks was observed.

X-ray Powder Diffractometry. X-ray diffraction patterns were obtained on D8 ADVANCE (Bruker AXS Gmbh, Germany). Samples were scanned in continuous mode from 4-45° (2θ) with step size of 0.02° on a spinning stage at 40 kV and 40 mA with Cu Kα radiation. The incident beam path was equipped with a 0.2 mm divergence slit and 0.02 mm air scattering screen. The diffracted beam was equipped with Ni-filter. Detection was accomplished with a Lynxeye (2.5) detector (Bruker AXS).

NMR. $^1$H Nuclear magnetic resonance (NMR) analysis was performed on Bruker Fourier 400 (Bruker) in deuterated solvent such as d-methanol at 25° C.

Infrad (IR) Analysis. IR analysis was conducted on Spectrum 100 FT-IR Spectrometer (Perkin Elmer) by use of the KBr pellet method.

Example 1

Production and Characterization of Co-Crystal of Kojic Acid and Maltol (1:1)

To a mixture of kojic acid (5.0 g, 35.2 mmol) and maltol (4.4 g, 35.2 mmol) at 65° C., 60 mL of MeOH was added until all powders were dissolved. The mixture was heated to 75° C., and MeOH was removed by evaporation until crystals began to form. Continued to evaporate the solvent (i.e., methanol) until its volume was reduced to about 40 mL. Then, the crystals were collected by filtration and vacuum dried at RT for 24 hours to give 6.6 g of kojic acid:maltol (1:1) co-crystal.

The thus obtained co-crystal was subjected to $^1$H-NMR, powder X-ray diffraction, thermoanalysis, and IR analyses, and the results were depicted in FIGS. 1 to 4. NMR analysis confirmed that the molecular ratio between kojic acid and maltol was about 1:1.

Characteristic peaks at 2θ(°) of the X-ray diffraction patterns of the co-crystal were as follows: 13.3; 14.0; 14.2; 14.7; 15.1; 15.4; 16.0; 16.3; 17.4; 17.8; 18.1; 19.3; 21.3; 21.6; 22.0; 23.6; 23.8; 25.3; 25.6; 26.6; 27.0; 27.2; 27.5; 28.0; 28.3; 29.1; 29.7; 30.3; 30.4; 30.8; 30.9; 32.2; 32.9; 33.1; 35.6; 35.7; 36.1; 37.3; 39.1; 39.2; 39.7; 39.8; 44.5; 44.7; 44.8.

$^1$H-NMR (400 MHz, MeOD): δ7.95 (s, 1H), 7.93 (d, J=8.0 Hz, 1H), 6.50 (s, 1H), 6.39 (d, J=8.0 Hz, 1H), 4.41 (s, 2H), 2.34 (s, 3H).

Example 2

Production and Characterization of Co-Crystal of Kojic Acid and Ethyl Maltol (2:1)

To a mixture of kojic acid (5.0 g, 35.2 mmol) and ethyl maltol (4.9 g, 35.2 mmol) at 65° C., 80 mL of MeOH was added until all powders were dissolved. The mixture was heated to 75° C., and MeOH was removed by evaporation until crystals began to form. Continued to evaporate the solvent (i.e., methanol) until its volume was reduced to about 50 mL. Then, the crystals were collected by filtration and vacuum dried at RT for 24 hours to give 6.1 g of kojic acid:ethyl maltol co-crystal.

The thus obtained co-crystal was subjected to $^1$H-NMR, powder X-ray diffraction, thermoanalysis, and IR analyses, and the results were depicted in FIGS. 5 to 8. NMR analysis confirmed that the molecular ratio between kojic acid and ethyl maltol was about 2:1.

Characteristic peaks at 2θ(°) of the X-ray diffraction patterns of the co-crystal were as follows: 8.6; 8.8; 13.4; 13.6; 14.2; 15.6; 17.7; 18.4; 19.2; 21.6; 22.0; 23.0; 23.2; 23.5; 24.7; 25.3; 26.4; 26.6; 26.9; 27.3; 27.6; 28.5; 28.6; 29.0; 29.7; 29.9; 30.1; 30.5; 30.6; 31.0; 31.9; 32.0; 32.1; 32.9; 33.8; 35.8; 36.2; 37.3; 39.1; 39.2; 39.9; 40.8; 41.6; 42.7; 42.8; 42.9; 43.5; 43.7; 44.0; 44.5; 44.8; 44.9.

$^1$H-NMR (400 MHz, MeOD): δ 7.96 (d, J=8.0 Hz, 1H), 7.95 (s, 2H), 6.50 (s, 2H), 6.39 (d, J=8.0 Hz, 1H), 4.41 (s, 4H), 2.76 (q, J=8.0 Hz, 2H), 1.24 (t, J=8.0 Hz, 3H).

Example 3

Production and Characterization of Eutectic Crystal of Kojic Acid and Maltol (2:1)

To a mixture of kojic acid (11.3 g, 79.4 mmol) and maltol (5.0 g, 39.7 mmol) at 65° C., 70 mL of MeOH was added until all powders were dissolved. The mixture was heated to 75° C., and MeOH was removed by evaporation until crystals began to form. Continued to evaporate the solvent (i.e., methanol) until its volume was reduced to about 50 mL. Then, the crystals were collected by filtration and vacuum dried at RT for 24 hours to give 3.7 g of kojic acid:maltol eutectic crystal.

The thus obtained eutectic crystal was subjected to $^1$H-NMR, powder X-ray diffraction, thermoanalysis, and IR analyses, and the results were depicted in FIGS. 9 to 12. NMR analysis confirmed that the molecular ratio between kojic acid and maltol was about 2:1.

Characteristic peaks at 2θ(°) of the X-ray diffraction patterns of the co-crystal were as follows: 14.0; 14.2; 14.7; 19.3; 21.0; 21.5; 22.0; 23.8; 25.3; 26.7; 27.0; 27.5; 27.6; 28.5; 29.1; 30.4; 31.1; 35.6; 35.7; 36.2; 37.4; 39.1; 39.2; 39.6; 41.4; 41.7; 42.8; 44.8; 44.9.

$^1$H-NMR (400 MHz, MeOD): δ 7.95 (s, 2H), 7.94 (d, J=4.0 Hz, 1H), 6.50 (s, 2H), 6.39 (d, J=4.0 Hz, 1H), 4.41 (s, 4H), 2.34 (s, 3H).

Example 4

Production and Characterization of Eutectic Crystal of Kojic Acid and Propyl Gallate (2:1)

To a mixture of kojic acid (5.0 g, 35.2 mmol) and propyl gallate (7.5 g, 35.2 mmol) at 65° C., 70 mL of MeOH was added until all powders were dissolved. The mixture was heated to 75° C., and MeOH was removed by evaporation until crystals began to form. Continued to evaporate the solvent (i.e., methanol) until its volume was reduced to about 50 mL. Then, the crystals were collected by filtration and vacuum dried at RT for 24 hours to give 4.6 g of kojic acid: propyl gallate eutectic crystal.

The thus obtained eutectic crystal was subjected to $^1$H-NMR, powder X-ray diffraction, thermoanalysis, and IR analyses, and the results were depicted in FIGS. 13 to 16. NMR analysis confirmed that the molecular ratio between kojic acid and propyl gallate was about 2:1.

Characteristic peaks at 2θ(°) of the X-ray diffraction patterns of the co-crystal were as follows: 4.3; 5.1; 5.6; 7.7; 10.2; 10.5; 11.0; 11.8; 13.5; 14.2; 14.8; 15.6; 16.1; 16.3; 16.5; 16.8; 17.2; 17.4; 17.8; 18.6; 19.3; 20.4; 20.7; 21.6; 21.9; 22.6; 23.2; 23.5; 23.8; 25.3; 25.9; 26.3; 26.7; 27.5; 28.5; 29.2; 30.0; 30.4; 31.0; 31.3; 32.1; 33.2; 33.8; 35.0; 35.7; 36.2; 37.4; 37.7; 38.3; 38.8; 39.1; 39.8; 41.6; 42.7; 42.8; 43.6; 44.8.

$^1$H-NMR (400 MHz, MeOD): δ 7.95 (s, 2H), 7.05 (s, 2H), 6.50 (s, 2H), 4.41 (s, 4H), 4.19 (t, J=8.0 Hz, 2H), 1.76 (sext, J=8.0 Hz, 2H), 1.03 (t, J=8.0 Hz, 3H).

Example 5

Production and Characterization of Eutectic Crystal of Kojic Acid and Methyl Paraben (2:1)

To a mixture of kojic acid (5.0 g, 35.2 mmol) and methyl paraben (5.4 g, 35.2 mmol) at 65° C., 80 mL of MeOH was added until all powders were dissolved. The mixture was heated to 75° C., and MeOH was removed by evaporation until crystals began to form. Continued to evaporate the solvent (i.e., methanol) until its volume was reduced to about 50 mL. Then, the crystals were collected by filtration and vacuum dried at RT for 24 hours to give 4.4 g of kojic acid:methyl paraben eutectic crystal.

The thus obtained eutectic crystal was subjected to $^1$H-NMR, powder X-ray diffraction, thermoanalysis, and IR analyses, and the results were depicted in FIGS. 17 to 20. NMR analysis confirmed that the molecular ratio between kojic acid and methyl paraben was about 2:1.

Characteristic peaks at 2θ(°) of the X-ray diffraction patterns of the co-crystal were as follows: 8.9; 9.1; 9.6; 10.0; 11.6; 13.7; 14.1; 14.2; 15.1; 15.3; 15.5; 16.6; 16.9; 17.1; 17.4; 17.9; 18.3; 18.5; 18.6; 19.0; 19.1; 19.3; 20.1; 21.0; 21.6; 22.0; 22.9; 23.9; 25.0; 25.1; 25.3; 25.6; 26.0; 26.2; 26.7; 27.6; 27.8; 28.5; 29.2; 29.5; 29.8; 30.5; 30.8; 30.9; 31.0; 31.9; 32.0; 32.2; 32.3; 33.2; 33.3; 33.9; 35.0; 35.5; 35.7; 35.8; 35.9; 36.0; 36.1; 36.4; 36.9; 37.5; 37.9; 38.8; 38.9; 39.2; 39.9; 41.6; 42.4; 42.6; 42.7; 42.8; 43.1; 43.5; 43.6; 44.1; 44.6; 44.9.

$^1$H-NMR (400 MHz, MeOD): δ 7.95 (s, 2H), 7.86 (d, J=8.0 Hz, 2H), 6.82 (d, J=8.0 Hz, 2H), 6.50 (s, 2H), 4.41 (s, 4H), 3.84 (s, 3H).

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A co-crystal of kojic acid and ethyl maltol characterized in having a powder X-ray diffraction pattern substantially as depicted in FIG. 5.

2. The co-crystal of claim 1, wherein the molecular ratio between kojic acid and ethyl maltol is about 2:1.

3. The co-crystal of claim 2, wherein the co-crystal has an endothermic peak corresponding to the melting point of about 88-90° C.

4. A process for producing the co-crystal of claim 1, comprising:
   (a) dissolving kojic acid and ethyl maltol at a first temperature to produce a molten;
   (b) adding a solvent in a drop-wise manner to the molten of the step (a) until a solution is formed;
   (c) heating the solution of the step (b) to a second temperature; and
   (d) cooling the heated solution of step (c) to ambient temperature to form the co-crystal of claim 1;
   wherein, the second temperature is higher than the first temperature.

5. A method for the treatment and/or prophylaxis of a subject having or suspected of having a neuropsychiatric disorder associated with D-amino acid oxidase (DAAO) comprising administering to the subject an effective amount of the co-crystal of claim 1 to ameliorate or prevent the symptoms of the neuropsychiatric disorder associated with DAAO.

6. The method of claim 5, wherein the neuropsychiatric disorder associated with DAAO is any of schizophrenia, anxiety, social anxiety disorder, panic disorder, pain, Alzheimer's disease, dementia, mild cognitive impairment, autism, Asperger's disorder, depression, attention deficit hyperactivity disorder, obsessive compulsive disorder, childhood learning disorders, closed head injury, premenstrual syndrome or bipolar disorder.

* * * * *